(12) United States Patent
Tickner

(10) Patent No.: US 6,858,848 B1
(45) Date of Patent: Feb. 22, 2005

(54) GAMMA-RAY IMAGING

(75) Inventor: James Richard Tickner, Erskineville (AU)

(73) Assignee: Commonwealth Scientific and Industrial Research Organisation, Campbell Actr (AU)

( * ) Notice: Subject to any disclaimer, the term of this patent is extended or adjusted under 35 U.S.C. 154(b) by 140 days.

(21) Appl. No.: 10/130,482
(22) PCT Filed: Nov. 14, 2000
(86) PCT No.: PCT/AU00/01393
§ 371 (c)(1), (2), (4) Date: Jul. 23, 2002
(87) PCT Pub. No.: WO01/36997
PCT Pub. Date: May 25, 2001

(30) Foreign Application Priority Data

Nov. 18, 1999 (AU) .............................................. PQ4142

(51) Int. Cl.⁷ .............................................. G01N 23/01
(52) U.S. Cl. .............................. 250/363.03; 250/370.09
(58) Field of Search ....................... 250/363.03, 363.04, 250/363.1, 363.02, 370.09, 370.1; 378/86, 87, 89, 90

(56) References Cited

U.S. PATENT DOCUMENTS

| | | | |
|---|---|---|---|
| 4,124,804 A | 11/1978 | Mirell | |
| 4,638,158 A | 1/1987 | Sonne et al. | |
| 5,430,787 A | 7/1995 | Norton | |
| 5,763,886 A | 6/1998 | Schulte | |
| 6,424,695 B1 * | 7/2002 | Grodzins et al. | ............. 378/87 |

* cited by examiner

Primary Examiner—Constantine Hannaher
Assistant Examiner—Timothy Moran
(74) Attorney, Agent, or Firm—Nixon & Vanderhye P.C.

(57) ABSTRACT

The specification describes an instrument and a method for determining information about an object (J), only one side of which is available for examination. The method involves exposing the object to gamma-rays and measuring the position and/or time of arrival of gamma-rays at a detector (D). The instrument includes a source of gamma-rays (S) located so that at least some gamma-rays impact upon the object, and a detector surrounded by a shield (C) having an aperture (A) for facing at the object to be studied. The detector is capable of measuring the position and/or time of arrival at the detector of gamma-rays passing through the aperture.

34 Claims, 4 Drawing Sheets

GAMMA-RAY IMAGING

This application is the US national phase of international application PCT/AU00/01393 filed 14 Nov. 2000, which designated the US.

TECHNICAL FIELD

The invention relates to the use of gamma-rays to produce an image of an object. In particular, the invention is useful in applications where a 1, 2 or 3-dimensional image is required and there is access to only one side of the object.

BACKGROUND ART

Gamma-rays are widely used to produce images of extended objects, for example for medical diagnoses. When there in access to both sides of the object being studied, the conventional approach is to measure the attenuation of a gamma-ray beam passing through the object from a source on one side of the object to a detector on the other. If a wide area beam is used together with a position sensitive detector, a two dimensional map of the object is produced. To produce a 3-dimensional image, multiple two dimensional slices can be combined using computed tomography (CT) techniques. If the object being studied can be injected with a positron emitting nuclide, positron emission tomography (PET) can be used to build up a 3-dimensional image of the object by using the back-to-back 511 keV gamma-rays produced when the positron annihilates.

Throughout the specification the term gamma-ray means electromagnetic photons having an energy of about 1 keV or more and includes electromagnetic photons normally known as X-rays which range up to about 100 keV.

When there is access to only one side of the object being studied, techniques based on gamma-ray transmission are impossible. Compton scatter imaging (CSI) has been proposed as an alternative method. Gamma-rays from a source pass into the object being studied, undergo a Compton scatter back out of the object and are counted using a suitable detector. Because there is a close relationship between the angle that the gamma-ray scatters through and the energy that it loses, by measuring the energy spectrum of the scattered gamma-rays it is possible to infer the distribution of material within the object of interest. However, unfolding this distribution requires complicated mathematical deconvolution techniques. Alternatively, if a collimated gamma-ray beam is used and the direction of the scattered gamma-rays is determined, direct imaging is possible. However, such systems typically have fairly low efficiencies and scanning is required to build up a full 3-dimensional image.

If the object being studied produces gamma-rays itself (examples would include a biological specimen injected with a radiological tracer or a distant astronomical image), a 2-dimensional image of the radioactive source density can be produced using an Anger camera or a Compton telescope. The former uses a position sensitive gamma-ray detector together with a gamma-ray opaque screen with a small aperture that projects an image of the object being studied onto the detector. Large or multiple apertures can be used to increase the efficiency of the camera, but necessitate the use of mathematical deconvolution techniques to form an image. The Compton telescope makes use of the angle/energy relationship of the Compton scattering process described above to infer the direction of an incident gamma-ray by measuring its interaction with two separate position sensitive detectors. The Compton telescope can be fairly efficient, but again mathematical deconvolution is required to obtain an image.

All of these methods suffer from one or more of the following disadvantages:
Access is required to 2 or more sides of the object being studied;
Only 2-dimensional information is obtained;
The object being studied needs to contain radioactive nuclei;
Complex mathematical techniques are required to produce an image of the object;
Scanning of the object and/or source/detector are required to build up an image.

SUMMARY OF THE INVENTION

In a first aspect, the invention provides an instrument for obtaining 2-dimensional information about the distribution of mass of an object, the instrument including;
a source of positrons, shielded so that the positrons annihilate and produce co-linear gamma-rays pairs in the immediate vicinity of the source, said source being located with respect to an object to be examined that at least some of the gamma-rays impinge on the object;
a gamma-ray shield surrounding a gamma-ray detector having an aperture for facing at the object to be examined, said gamma-ray detector being located on the same side of the object as the source of positrons, and said gamma-ray detector being capable of detecting the arrival position of gamma-rays of said gamma-ray pairs travelling directly from the source and the arrival position of gamma-rays of said gamma-ray pairs after scattering from the object and passing through said aperture; and
means for determining 2-dimensional information about the object from the direction of flight of the directly detected gamma-ray and the arrival position of the scattered gamma-ray of each gamma-ray pair.

In a second aspect, the invention provides an instrument for obtaining 2-dimensional information about the distribution of mass of an object, the instrument including:
a source of gamma-rays so located with respect to an object to be examined that at least some of the gamma-rays impinge on the object;
a gamma ray shield surrounding a gamma-ray detector having an aperture for facing at the object to be examined said aperture being sufficiently small to project an image of the object onto said detector, said gamma-ray detector being located on the same side of the object as the source of gamma-rays and being capable of detecting the arrival position of gamma-rays scattered from the object and passing through the aperture; and
means for determining 2-dimensional information about the object derived from the detected positions of scattered gamma-rays.

In a third aspect, the invention provides an instrument for obtaining 1-dimensional information about the distribution of mass of an object, the instrument including:
a source of gamma-rays, said source being so located with respect to an object to be examined that at least some of the gamma-rays impinge on the object;
a gamma-ray shield surrounding one or more detectors having an aperture for facing at the object to be examined;
a detector located on the same side of the object as said source, said detector being capable of determining the arrival time of gamma-rays having scattered from the object and inferring the departure time of said gamma-rays from said source; and means for determining 1-dimensional information about the object from the arrival times of said scattered gamma-rays and said inferred departure times of said gamma-rays.

In a fourth aspect, the invention provides a method for obtaining 2-dimensional information about the distribution of mass of an object, the method including:

generating co-linear gamma-ray pairs using a position source;

causing at least some of the gamma-rays to impact on an object;

detecting the position of arrival of each gamma-ray pair incident upon a detector located on the same side the object as said source; and determining 2-dimensional information about the object from the direction of flight of the directly detected gamma-ray and the arrival position of the scattered gamma-ray of each gamma-ray pair.

In a fifth aspect, the invention provides a method for obtaining 2-dimensional information about the distribution of a mass of an object, the method including:

generating gamma-rays using a gamma-ray source;

causing at least some of the gamma-rays to impact on an object;

shielding a detector located on the same side of the object as said gamma-ray source with a shield having a aperture having a size sufficiently small enough to project an image of the object onto said detector;

detecting the position of each gamma-ray scattered from the object incident upon said detector; and determining 2-dimensional information about the object from the detected position of the scattered gamma-rays.

In a sixth aspect, the invention provides a method for obtaining 1-dimensional information about the distribution of mass of an object, the method including:

generating gamma-rays using a gamma-ray source;

causing at least some of the gamma-rays to impact on an object;

determining the arrival times at said detector of gamma-rays having scattered from said object;

inferring departure times of said to be scattered gamma-rays from said source; and determining 1-dimensional information about the object from the arrival times of said scattered gamma-rays and the inferred departure times of said to be scattered gamma-rays.

DETAILED DESCRIPTION OF THE DRAWINGS

Figure 1:
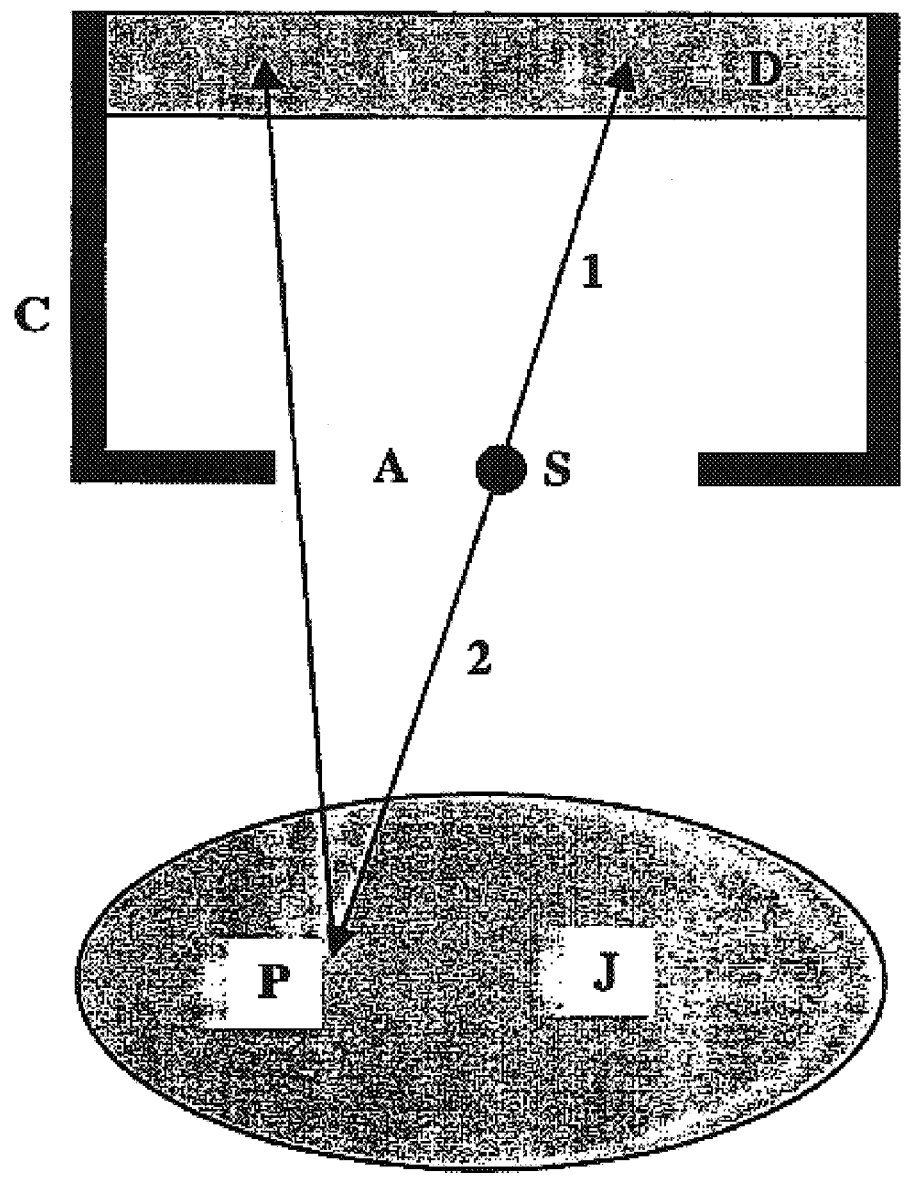
FIG. 1 is a schematic drawing of a preferred embodiment of the invention.

FIG. 1 shows: (i) a gamma-ray detector (D) which is instrumented to provide the position and time of an incident gamma-ray; (ii) a collimator (C) made of lead or another suitable gamma-ray shielding material containing an aperture (A) in its front face and (iii) a positron source (S) surrounded by sufficient shielding material that positrons emitted by the source are brought to rest and annihilate in the vicinity of the source.

The operation of the embodiment is as follows. A positron from the source (S) comes to rest in the shielding surrounding the source and annihilates, producing two 511 keV gamma-rays travelling back-to-back. One of the gamma-rays (1) is detected in detector (D) and the time and position of its arrival noted. The other gamma-ray (2) enters the object being examined (J) and scatters at some point (P) within the object. The scattered gamma-ray is then detected in detector (D) and its position and time of arrival noted. The positions of the two gamma-rays in detector (D) and the time between their arrival suffices to calculate the scattering position (P). By measuring gamma-rays free a large number of positron annihilation events, a profile of the probability of scattering and hence the electron-density inside the object (J) can be determined. The electron density in turn can be approximately related to the physical density of matter inside the object.

Figure 2:
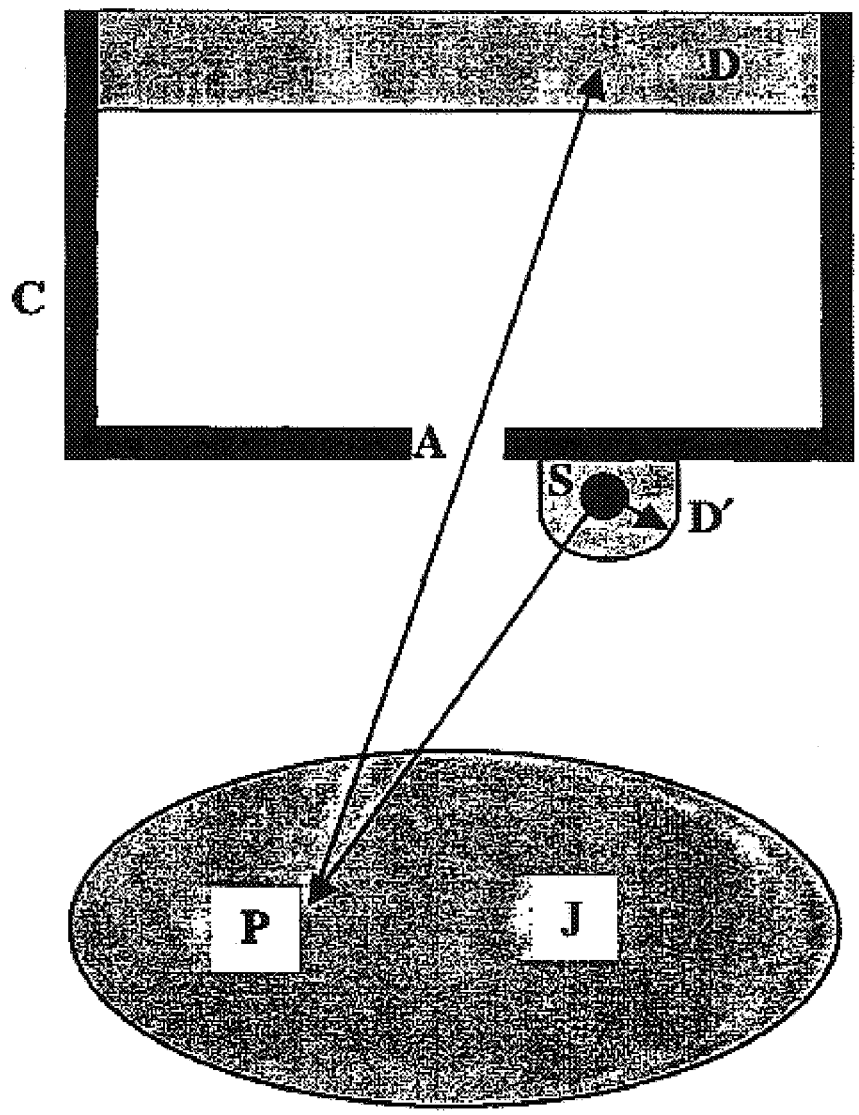
FIG. 2 is a schematic drawing of a second embodiment of the invention.

FIG. 2 depicts a gamma-ray source (S) producing 2 or more coincident gamma-rays, gamma-ray detectors (D and D'), and a collimator (C) containing an aperture (A). Gamma-ray (1) is detected in (D') travelling directly from the source and gamma-ray (2) is detected in (D) after scattering at point (P) in the object being studied (J). Gamma-ray detector (D') can be omitted, with both gamma-rays being detected in detector (D).

Figure 3:
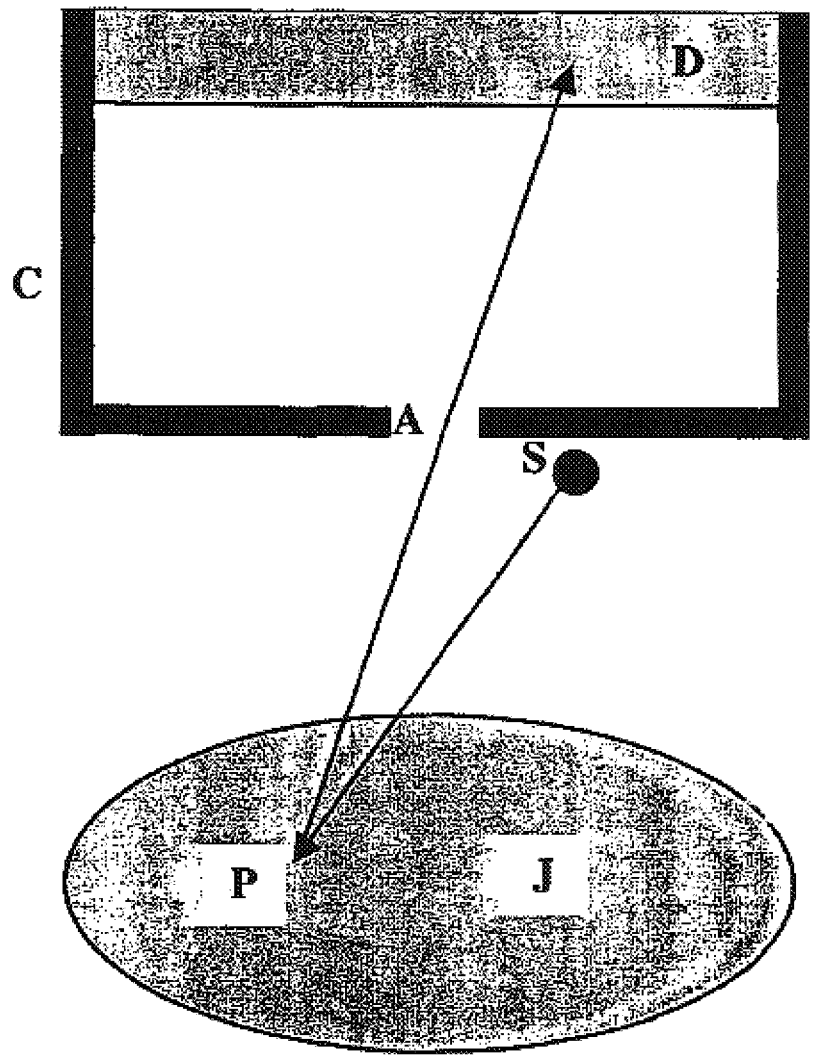
FIG. 3 is a schematic drawing of a third embodiment of the invention.

FIG. 3 depicts a gamma-ray source (S), gamma-ray detector (D), and a collimator (C) containing an aperture (A). Gamma-rays are detected in (D) after scattering at point (P) in the object being studied (J).

Figure 4:
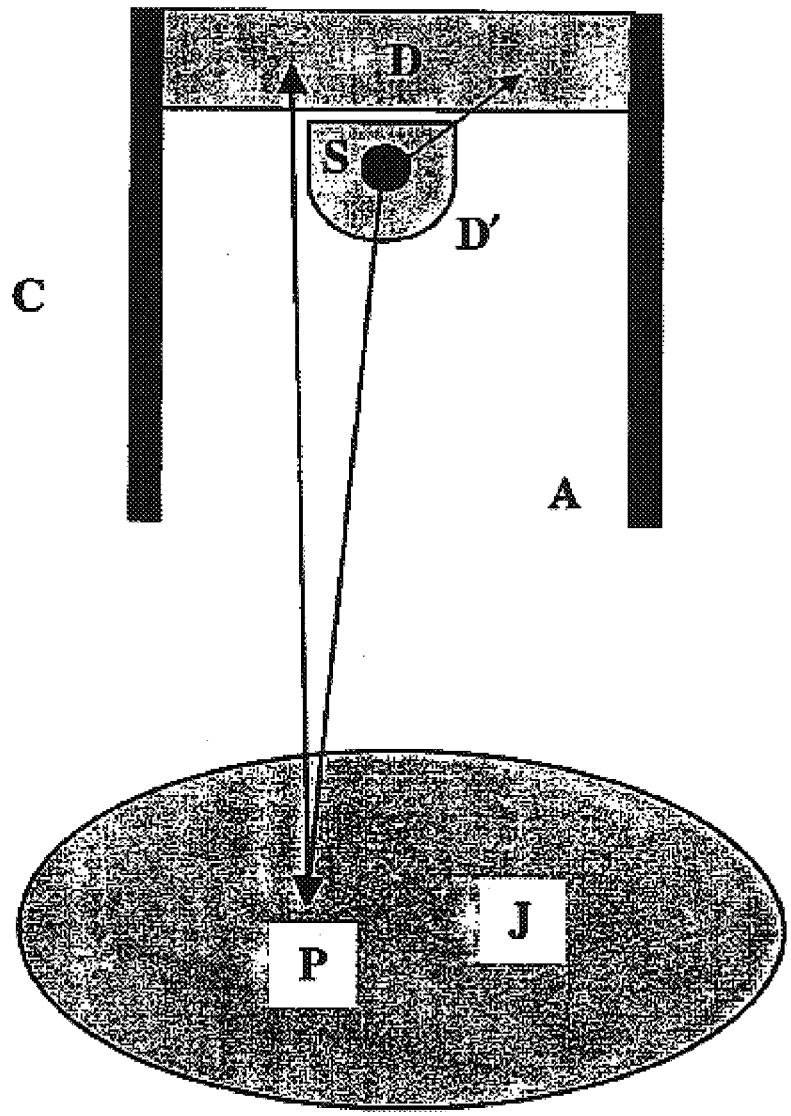
FIG. 4 is a schematic drawing of another embodiment of the invention.

FIG. 4 depicts a gamma-ray or positron source (S) producing 2 or more coincident gamma-rays, gamma-ray detectors (D and D'), and a collimator (C) containing an aperture (A). One gamma-ray is detected directly in detector (D) or (D') if used; the other gamma-ray is detected in (D) after scattering at point (P) in the object being studied (J). Gamma-ray detector (D') can be omitted, with both gamma-rays being detected in detector (D).

MODES FOR CARRYING OUT THE INVENTION

The physical dimensions and construction of the embodiments depend on the spatial resolution that is required when mapping the density of object (J) and the field of view required.

Detector (D) may comprise one or more slabs of a scintillator material having a fast light decay time. The slab(s) are read out by a multiplicity of light detectors such as photomultiplier tubes or semiconductor diodes. Timing and possibly amplitude information from these detectors may be used to determine the position and arrival time of an incident gamma-ray. It will be appreciated that this description represents only one possible realisation of detector (D) and other detectors designs could be used without affecting the underlying nature of the invention.

The collimator (C) should be sufficiently opaque to gamma-rays to shield the detector (D) from gamma-rays scattered from the object (J), other than those gamma-rays passing through aperture (A). The size and form of aperture (A) should be chosen to optimize the spatial resolution and efficiency of the invention.

The following variations on the first embodiment are also included:

1. A gamma-ray imaging device as per the first embodiment, with the positron source (S) replaced by a gamma-ray source which produces at least two coincident gamma-rays per decay. One gamma-ray is detected in detector (D) or in a small detector (D') immediately surrounding the source (S) and its time of arrival noted. The other gamma ray scatters from th object (J) and its time and arrival in detector (D) noted. Aperture (A) is made mall enough that scattered gamma-rays project an image of object (J) onto detector (D). From the position of the scattered gamma-ray in detector (D) and the time between its arrival and the arrival of the directly detected gamma-ray, the scattering position (P) and hence the density profile of the object (J) can be determined. By selecting a source producing gamma-rays of suitable energy, the penetration of the imaging device into object (J) can be controlled.

2. A gamma-ray imaging device as per the second embodiment, with the source (S) replaced by a gamma-ray source where only one gamma-ray per decay is used. No timing information is measured or used. Such a device would permit a 2-dimensional map of the density of object (J) to be determined, with the density profile over the third coordinate (radial distance from the source (S)) being averaged.

3. A gamma-ray profiling device as per the first embodiment, with the arrival position of the two gamma-rays in detector (D) not being measured or used. The difference between the arrival times of the two gamma-rays is used to determine the density profile of object (J) in 1-dimension (radial distance from the source (S)). The source (S) can either comprise a positron emitting source as in the main invention, or a source producing two coincident gamma-rays as per variation 1 above; in this instance, one of the gamma-rays may be detected in a small detector (D') surrounding the source. Collimator (C) and aperture (A) can be adjusted to control the transverse size of the region of object (J) that is examined.

FIGS. 2, 3 and 4 illustrate these variations. Other minor variations, within the spirit of the main invention and the variations described above, are also included within the scope of the invention.

Industrial Applicability

The invention has utility in the following applications:
1. Detection of buried landmines relying on the fact that mines have a different density from the surrounding soil.
2. Detection of other buried objects having dimensions a few cm or larger.
3. Non-invasive measurement of refractory linings inside burners or furnaces.
4. Non-invasive measurement of the build up of deposits/scale inside pipelines.
5. Non-invasive measurement of density of materials flowing inside pipelines.

Other uses of the invention are also conceivable.

The claims defining the invention are as follows:

1. An instrument for obtaining 2-dimensional information about the distribution of mass of an object, the instrument including;
   a source of positrons, shielded so that the positrons annihilate and produce co-linear gamma-rays pairs in the immediate vicinity of the source, said source being located with respect to an object to be examined that at least some of the gamma-rays impinge on the object;
   a gamma-ray shield surrounding a gamma-ray detector having an aperture for facing at the object to be examined, said gamma-ray detector being located on the same side of the object as the source of positrons, and said gamma-ray detector being capable of detecting the arrival position of gamma-rays of said gamma-ray pairs travelling directly from the source and the arrival position of gamma-rays of said gamma-ray pairs after scattering from the object and passing through said aperture; and
   means for determining 2-dimensional information about the object from the direction of flight of the directly detected gamma-ray and the arrival position of the scattered gamma-ray of each gamma-ray pair.

2. An instrument as claimed in claim 1, wherein said gamma-ray detector is also capable of detecting the time of arrival of said gamma-rays, whereby the difference in arrival times between the scattered gamma-ray at the detector and its inferred departure time from the source is used to additionally infer the distance of penetration of the scattering gamma-ray into the object, whereby 3-dimensional information about the distribution of mass of an object can be obtained.

3. An instrument as claimed in claim 2, wherein the departure time of said scattered gamma-ray is inferred from the detection of a gamma-ray travelling directly from said source.

4. An instrument as claimed in claim 1, wherein said instrument includes two or more detectors and separate detectors are used to detect scattered gamma-rays and directly arriving gamma-rays.

5. An instrument as claimed in claim 1, wherein the detector consists of one or more slabs of a scintillator material which are read out by a multiplicity of light detectors.

6. An instrument according to claim 5, wherein the light detectors are photomultipliers or semi-conductor diodes having a fast response time.

7. An instrument according to claim 1, wherein a digital processing system is used to calculate and tabulate the inferred gamma-ray scattering positions within the object from at least one of the arrival positions and arrival times of the detected gamma-rays.

8. An instrument according to claim 7, wherein said digital processing system is used to calculate the distribution of mass within the object being examined from the tabulated gamma-ray scattering positions.

9. An instrument for obtaining 2-dimensional information about the distribution of mass of an object, the instrument including:
   a source of gamma-rays so located with respect to an object to be examined that at least some of the gamma-rays impinge on the object;
   a gamma ray shield surrounding a gamma-ray detector having an aperture for facing at the object to be examined said aperture being sufficiently small to project an image of the object onto said detector, said gamma-ray detector being located on the same side of the object as the source of gamma-rays and being capable of detecting the arrival position of gamma-rays scattered from the object and passing through the aperture; and
   means for determining 2-dimensional information about the object derived from the detected positions of scattered gamma-rays.

10. A instrument as claimed in claim 9, wherein said gamma-ray detector is also capable of detecting the time of arrival of said gamma-rays, whereby the difference in arrival times between the scattered gamma-ray at the detector and its inferred departure time from the source is used to additionally infer the distance of penetration of the scattering gamma-ray into the object, whereby 3-dimensional information about the distribution of mass of an object can be obtained.

11. An instrument as claimed in claim 10, wherein the departure time of said scattered gamma-ray is inferred from the detection of a gamma-ray travelling directly from said source.

12. An instrument as claimed in claim 9, wherein said instrument includes two or more detectors and separate detectors are used to detect scattered gamma-rays and directly arriving gamma-rays.

13. An instrument as claimed in claim 9, wherein the detector consists of one or more slabs of a scintillator material which are read out by a multiplicity of light detectors.

14. An instrument according to claim 13, wherein the light detectors are photomultipliers or semi-conductor diodes having a fast response time.

15. An instrument according to claim 9, wherein a digital processing system is used to calculate and tabulate the inferred gamma-ray scattering positions within the object from at least one of the arrival positions and arrival times of the detected gamma-rays.

16. An instrument according to claim 15, wherein said digital processing system is used to calculate the distribution of mass within the object being examined from the tabulated gamma-ray scattering positions.

17. An instrument for obtaining 1-dimensional information about the distribution of mass of an object, the instrument including:
  a source of gamma-rays, said source being so located with respect to an object to be examined that at least some of the gamma-rays impinge on the object;
  a gamma-ray shield surrounding one or more detectors having an aperture for facing at the object to be examined;
  a detector located on the same side of the object as said source, said detector being capable of determining the arrival time of gamma-rays having scattered from the object and inferring the departure time of said gamma-rays from said source; and
  means for determining 1-dimensional information about the object from the arrival times or said scattered gamma-rays and said inferred departure times of said gamma-rays.

18. An instrument as claimed in claim 17, wherein the departure time of said scattered gamma-ray is inferred from the detection of a gamma-ray travelling directly from said source.

19. An instrument as claimed in claim 17, wherein said instrument includes two or more detectors and separate detectors are used to detect scattered gamma-rays and directly arriving gamma-rays.

20. An instrument as claimed in claim 17, wherein the detector consists of one or more slabs of a scintillator material which are read out by a multiplicity of light detectors.

21. An instrument according to claim 20, wherein the light detectors are photomultipliers or semi-conductor diodes having a fast response time.

22. An instrument according to claim 17, wherein a digital processing system is used to calculate and tabulate the inferred gamma-ray scattering positions within the object from at least one of the arrival positions and arrival times of the detected gamma-rays.

23. An instrument according to claim 22, wherein said digital processing system is used to calculate the distribution of mass within the object being examined from the tabulated gamma-ray scattering positions.

24. A method for obtaining 2-dimensional information about the distribution of mass of an object, the method including:
  generating co-linear gamma-ray pairs using a position source;
  causing at least some of the gamma-rays to impact on an object;
  detecting the position of arrival of each gamma-ray pair incident upon a detector located on the same side of the object as said source; and
  determining 2-dimensional information about the object from the direction of flight of the directly detected gamma-ray and the arrival position of the scattered gamma-ray of each gamma-ray pair.

25. A method as claimed in claim 24, further including detecting the time of arrival of each gamma-ray, whereby the difference in arrival times between the scattered gamma-ray and its inferred departure time from the source is used to additionally infer the distance of penetration of the scattering gamma-ray into the object whereby 3-dimensional information about the distribution of mass of an object can be obtained.

26. A method as claimed in claim 25, wherein inferring departure times of said to be scattered gamma-rays involves determining arrival times of gamma-rays travelling directly from said source.

27. A method as claimed in claim 24, involving detecting scattered gamma-rays and directly arriving gamma-rays using separate detectors.

28. A method for obtaining 2-dimensional information about the distribution of a mass of an object, the method including:
  generating gamma-rays using a gamma-ray source;
  causing at least some of the gamma-rays to impact on an object;
  shielding a detector located on the same side of the object as said gamma-ray source with a shield having a aperture having a size sufficiently small enough to project an image of the object onto said detector;
  detecting the position of each gamma-ray scattered from the object incident upon said detector; and
  determining 2-dimensional information about the object from the detected position of the scattered gamma-rays.

29. A method as claimed in claim 28, further including detecting the time of arrival of each gamma-ray, whereby the difference in arrival times between the scattered gamma-ray and its inferred departure time from the source is used to additionally infer the distance of penetration of the scattering gamma-ray into the object whereby 3-dimensional information about the distribution of mass of an object can be obtained.

30. A method as claimed in claim 29, wherein inferring departure times of said to be scattered gamma-rays involves determining arrival times of gamma-rays travelling directly from said source.

31. A method as claimed in claim 28, involving detecting scattered gamma-rays and directly arriving gamma-rays using separate detectors.

32. A method for obtaining 1-dimensional information about the distribution of mass of an object, the method including:
  generating gamma-rays using a gamma-ray source;

causing at least some of the gamma-rays to impact on an object;

determining the arrival times at said detector of gamma-rays having scattered from said object;

inferring departure times of said to be scattered gamma-rays from said source; and determining 1-dimensional information about the object from the arrival times of said scattered gamma-rays and the inferred departure times of said to be scattered gamma-rays.

33. A method as claimed in claim 32, wherein inferring departure times of said to be scattered gamma-rays involves determining arrival times of gamma-rays travelling directly from said source.

34. A method as claimed in claim 32, involving detecting scattered gamma-rays and directly arriving gamma-rays using separate detectors.

* * * * *